United States Patent [19]

Alcaraz et al.

[11] Patent Number: 5,191,087
[45] Date of Patent: Mar. 2, 1993

[54] PROCESS FOR THE SYNTHESIS OF 1,4-DISUBSTITUTED PYRAZOLES

[75] Inventors: Jean-Marie Alcaraz, Saint Germain Les Corbeil; Maryse Lecacheur, Bergerac; Yves Robin, Vert Le Petit, all of France

[73] Assignee: Societe Nationale Des Poudres Et Explosifs, Paris, France

[21] Appl. No.: 914,574

[22] Filed: Jul. 20, 1992

[30] Foreign Application Priority Data

Jul. 24, 1991 [FR] France ................. 91 09331

[51] Int. Cl.$^5$ ........................... C07D 231/12
[52] U.S. Cl. ................. 548/373.1; 548/377.1
[58] Field of Search ........................ 548/373

[56] References Cited

FOREIGN PATENT DOCUMENTS 366328   5/1990  European Pat. Off. .
1022413  1/1958  Fed. Rep. of Germany .
1234223  2/1967  Fed. Rep. of Germany .

Primary Examiner—Robert W. Ramsuer
Attorney, Agent, or Firm—Cushman, Darby & Cushman

[57] ABSTRACT

The present invention relates to a process for the synthesis of 1,4-disubstituted pyrazoles. A monosubstituted hydrazine is reacted with the product of reaction of an acetal with an N-substituted halomethyliminium salt, preferably N,N-dimethylchloromethyliminium chloride.

The 1,4-disubstituted pyrazoles are, in particular, important intermediates in the synthesis of herbicides or drugs.

14 Claims, No Drawings

PROCESS FOR THE SYNTHESIS OF 1,4-DISUBSTITUTED PYRAZOLES

The present invention relates to a new process for the synthesis of 1,4-disubstituted pyrazoles.

1,4-Disubstituted pyrazoles are, in particular, important intermediates in the synthesis of herbicides or drugs.

Patent EP 366,328 describes the synthesis of N-substituted 4-methylpyrazoles by reaction of 2,3-dichloro-2-methylpropanal with a monosubstituted hydrazine. This process is, on the one hand, limited to 4-methyl derivatives and, on the other hand, it uses toxic compounds.

Patent DE 1,234,223 describes the synthesis of 1,4-disubstituted pyrazoles by reaction of a monosubstituted hydrazine with the product of reaction of an N-vinylamine with the product of reaction of phosgene with dimethylformamide (DMF). The substituent in position 4 cannot be an aromatic group, and this limits the applications. In addition, N-vinylamines are toxic and difficult to obtain, and this limits the industrial implementation of such a process, both insofar as the operation is concerned and insofar as the cost and effluent treatment are concerned.

The person skilled in the art is therefore searching for a process which can be made industrial and which is less costly than those mentioned above, employing readily accessible and nontoxic raw materials, which can be applied generally to all 1,4-disubstituted pyrazoles.

The present invention proposes such a process. It is characterised in that a monosubstituted hydrazine is reacted with the product of reaction of an acetal with an N-substituted halomethyliminium salt The acetals are nontoxic, cheap common products which are readily accessible, for example by reaction of an alcohol and an aldehyde which are basic raw materials in the chemical industry.

The process according to the invention is simple to operate, cheap, and can be applied generally to all 1,4-disubstituted pyrazoles, which can be obtained directly by a "one-pot" reaction employing 3 raw materials, without isolating any intermediate. The chemical nature of these raw materials and the product itself are such that the treatment of effluents does not present any special problem.

According to the invention a "mono-substituted hydrazine" means a compound obtained by substitution of one, and only one, hydrogen atom of hydrazine $NH_2-NH_2$ by an organic radical.

Furthermore, the halomethyliminium salt is N-substituted, that is to say that the quaternary iminium nitrogen atom $>N^{\oplus}=C<$ is linked to one (N-monosubstituted) or two (N,N-disubstituted) organic radicals, which excludes $H_2N^{\oplus}=C<$.

Preferably, according to the invention, 1,4-disubstituted pyrazoles of the general formula (III)

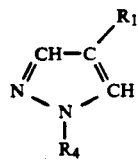

are obtained from acetals of general formula (I)

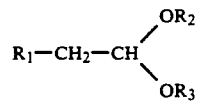

and from monosubstituted hydrazines of general formula (II)

$R_4NH-NH_2$, in which formulae (I), (II) and (III):
  $R_1$ and $RW_4$, which are identical or different, denote:
    a substituted or unsubstituted, linear or branched, aliphatic, preferably $C_1-C_{24}$ alkyl, radical,
    a substituted or unsubstituted aryl, preferably phenyl or naphthyl, radical,
  $R_2$ and $R_3$, which are identical or different, denote a substituted or unsubstituted, linear or branched, aliphatic, preferably $C_1-C_{24}$ alkyl, radical, or else $R_2$ and $R_3$, together with the 2 oxygen atoms to which they are linked and the carbon atom situated between these 2 oxygen atoms, form a substituted or unsubstituted ring preferably containing 3 to 49 carbon atoms.

$R_1$ and $R_4$, which are identical or different, preferably denote a $C_1-C_{12}$, preferably $C_1-C_4$, alkyl radical or a phenyl radical, optionally substituted.

Also preferably, $R_2$ and $R_3$, which are identical or different, denote a $C_1-C_{12}$, preferably $C_1-C_4$, alkyl radical, or else $R_2$ and $R_3$, together with the two oxygen atoms to which they are linked and the carbon atom situated between these two oxygen atoms, form a ring containing 3 to 7 carbon atoms, for example a 1,3-dioxolane ring.

According to a preferred alternative form of the invention the N-substituted halomethyliminium salt is an N-substituted, generally N,N-disubstituted, halomethyliminium halide preferably corresponding to the general formula (IV):

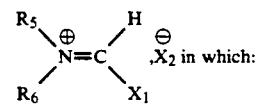

$X_1$ and $X_2$, which are identical or different, denote a chlorine or bromine atom,
$R_5$ denotes:
  a substituted or unsubstituted, linear or branched, aliphatic, preferably $C_1-C_{24}$ alkyl, radical,
  a substituted or unsubstituted aryl, preferably phenyl or naphthyl, radical,
$R_6$ denotes:
  hydrogen,
  a substituted or unsubstituted, linear or branched, aliphatic, preferably $C_1-C_{24}$ alkyl, radical,
  a substituted or unsubstituted aryl, preferably phenyl or naphthyl, radical,
  or else $R_5$ and $R_6$, together with the nitrogen atom to which they are linked, form a substituted or unsubstituted ring containing 3 to 48 carbon atoms, preferably 3 t 8 carbon atoms.

According to a particularly preferred alternative form, the N-substituted halomethyliminium halide is an N-substituted, preferably N,N-disubstituted, chloromethyliminium chloride, preferably obtained in situ in the reaction mixture by reaction of at least one halogenating agent with an N-substituted amide. As examples of halogenating agents there may be mentioned brominating agents such as COBr$_2$ and chlorinating agents such as COCl$_2$, (COCl)$_2$, SOCl$_2$ and mixtures thereof. Phosgene is particularly preferred.

The reaction between the acetal and the Nsubstitute halomethyliminium salt is generally carried out in an organic solvent medium, but can also take place in the absence of solvent. As examples of solvents which can be applied there may be mentioned optionally halogenated aliphatic hydrocarbons and optionally halogenated aromatic hydrocarbons, for example those of the ether or amide type.

The reaction temperature is generally between 20° and 150° C., preferably in the neighbourhood of 70° C.

After reaction between the acetal and the N-substituted halomethyliminium salt, and preferably without isolating the product of this reaction, the monosubstituted hydrazine is added pure in aqueous solution or in solution in an organic solvent. The operation can be carried out in reverse order, that is to say by adding the product of reaction of the acetal with the N-substituted halomethyliminium salt to the hydrazine.

When the reaction between the acetal and the N-substituted halomethyliminium salt takes place in the presence of an organic solvent, it is unnecessary to remove the latter before the addition of the monosubstituted hydrazine, but this can nevertheless be done After the addition of the monosubstituted hydrazine the temperature is generally maintained between 40° and 150° C., preferably at approximately 70° C.

The duration of each of these 2 stages of the process according to the invention is generally between 0.5 h and 4 h, preferably in the neighbourhood of 2 h.

The reaction mixture is then neutralised with a basic aqueous solution, for example sodium hydroxide, potassium hydroxide, alkali metal carbonate or aqueous ammonia, to allow the 1,4-disubstituted pyrazole formed to be subsequently extracted with an organic solvent.

After evaporation of the extraction solvent the pure 1,4-disubstituted pyrazole can be recovered from the crude product, for example by distillation under reduced pressure or by recrystallisation. Unexpectedly, a product of greater purity is obtained when the crude product is treated beforehand with a concentrated (for example 30%) alkaline aqueous solution, with heating, for example 40° C. to 70° C. A treatment for 1 h generally suffices. The residual DMF content can thus be lower than 0.5% by weight, and this is particularly advantageous. Other byproducts of the synthesis are also removed in this way.

The molar ratio of the N-substituted halomethyliminium salt to the acetal is generally between 1.5 and 3, preferably in the neighbourhood of 2, and the molar ratio of the monosubstituted hydrazine to the acetal is generally between 0.8 and 2, preferably in the neighbourhood of 1.

When the N-substituted halomethyliminium salt is an N-substituted halomethyliminium halide obtained in situ in the reaction mixture by reaction of at least one halogenating agent with an N-substituted amide, the molar ratio of the halogenating agent to the acetal is generally between 1.4 and 4, preferably in the neighbourhood of 2, the molar ratio of the N-substituted amide to the acetal is generally between 0.8 and 3, preferably in the neighbourhood of 1, and the molar ratio of the mono- substituted hydrazine to the acetal is between 0.8 and 2, preferably in the neighbourhood of 1.

The following nonlimiting examples illustrate the invention and some of the advantages which it provides.

EXAMPLE 1

Synthesis of 1,4-dimethylpyrazole from propionaldehyde diethyl acetal, N,N-dimethylchloromethyliminium chloride and monomethylhydrazine.

116.2 g (0.88 mol) of propionaldehyde diethyl acetal at a temperature of between 25° C. and 55° C. are introduced into a reactor containing 226.6 g (1.77 mol) of N,N-dimethylchloromethyliminium chloride in solution in 400 ml of chloroform and the solution is then heated to 55° C. for 2 h. The chloroform is removed under reduced pressure and 44.5 g (0.97 mol) of monomethylhydrazine in aqueous solution at a concentration of 30% are then introduced at 50° C. The solution is heated for 2 h at 75° C. The reaction mixture is cooled to 20° C. and an aqueous solution of sodium hydroxide is then added to pH =8. 100 ml of water are then added and the required product is then extracted with 3 25-ml portions of chloroform. The extraction solvent is removed under reduced pressure and the residue is then heated for 1 h to 50° C. in the presence of 30% sodium hydroxide solution. The 1,4-dimethylpyrazole formed is recovered by phase separation. After drying, followed by purification by distillation under reduced pressure, 56.6 g (0.59 mol) of pure 1,4-dimethylpyrazole are obtained. The yield of isolated product is 67%.

EXAMPLE 2

Synthesis of 1,4-dimethylpyrazole from 2-ethyl-1,3-dioxolane, N,N-dimethylchloromethyliminium chloride and monomethylhydrazine.

40.8 g (0.4 mol) of 2-ethyl-1,3-dioxolane at a temperature of between 50° C. and 70° C. are introduced into a reactor containing 102.4 g (0.80 mol) of N,N-dimethylchloromethyliminium chloride in solution in 400 ml of chloroform and the solution is then heated for 2 h to 75° C. The chloroform is removed under reduced pressure and 18.9 g (0.41 mol) of monomethylhydrazine in aqueous solution at a concentration of 30 % are then introduced at 50° C. The solution is heated for 2 h at 75° C. The reaction mixture is cooled to 20° C. and an aqueous solution of sodium hydroxide is then added to pH =8. 40 ml of water are then added and the required product is then extracted with 2 20-ml portions of chloroform. The extraction solvent is removed and the residue is then hydrolysed by heating for 1 h at 50° C. in the presence of 30% sodium hydroxide solution. The 1,4-dimethylpyrazole is recovered by phase separation and is then dried and purified by distillation under reduced pressure. The yield of isolated pure product is 72%. The yield of product formed, obtained by determination in the crude product, is 90%.

EXAMPLE 3

Synthesis of 1,4-dimethylpyrazole from propionaldehyde diethyl acetal, N,N-dimethylchloromethyliminium chloride generated in situ from DMF and phosgene, and monomethylhydrazine.

50 g (0.5 mol) of phosgene are introduced at 10° C. into a reactor containing 310 ml of chloroform, 29.2 g (0.4 mol) of DMF and 56.8 g (0.43 mol) of propionaldehyde diethyl acetal. The reaction mixture is heated to 30° C. and 56 g (0.55 mol) of phosgene are then introduced gradually over approximately 1.5 h at a temperature of between 30° C. and 50° C. The reaction is extended for 0.5 at 50° C. 21.7 g (0.47 mol) of monomethylhydrazine in aqueous solution at a concentration of 30% are then introduced at 30° C. The materials are left to react for 2 h at 75° C. The mixture is allowed to cool and the aqueous phase is then recovered after phase separation. This aqueous phase is neutralised with an aqueous 30% sodium hydroxide solution to pH =7. The aqueous phase is extracted with 3 75-ml portions of chloroform and the organic phases are then concentrated to obtain 70.5 g of crude product containing 30.3 g of pure 1,4-dimethylpyrazole (73% yield) whose residual DMF content is lower than 0.3%.

EXAMPLE 4

Synthesis of 1,4-dimethylpyrazole from 2-ethyl-1,3-dioxolane, N-methyl-N-phenylchloromethyliminium chloride generated in situ from phosgene and N-methylformanilide, and monomethylhydrazine.

50 g (0.50 mol) of phosgene are introduced, at a temperature of 70° C., into a reactor containing 80 ml of toluene, 27 g (0.20 mol) of N-methylformanilide and 0.5 g (0.20 mol) of 2-ethyl-1,3-dioxolane. The materials are left to react for 3 h at 70° C. The mixture is cooled to 50° C. and 9.2 g (0.20 mol) of monomethylhydrazine in aqueous solution at a concentration of 30% are then introduced at a temperature of between 50° C. and 75° C. The mixture is heated for 2 h at 75° C. It is cooled to 20° C. and then neutralised to pH =8 with an aqueous 30% sodium hydroxide solution. 20 ml of water are added and the organic phase, which contains 13 g of pure 1,4-dimethylpyrazole (70% yield) is then recovered by phase separation.

EXAMPLE 5

Synthesis of 1-phenyl-4-methylpyrazole from 2-ethyl-1,3-dioxolane, N,N-dimethylchloromethyliminium chloride and monophenylhydrazine.

25 g (0.25 mol) of 2-ethyl-1,3-dioxolane are introduced, at a temperature of between 45° C. and 60° C., into a reactor containing 67.37 g (0.526 mol) of N,N-dimethylchloromethyliminium chloride in solution in 175 ml of chloroform. The solution is heated for 1 h to 60° C. The chloroform is removed under reduced pressure and 30 g (0.267 mol) of monophenylhydrazine in chloroform solution at a concentration of 30% are then introduced at 50° C. The solution is heated for 2 h at 70° C. It is cooled to 20° C. and an aqueous sodium hydroxide solution is then added to pH =8. 25 ml of water are then added and the required product is then extracted with 2 20-ml portions of chloroform. The extraction solvent is removed and the residue is then hydrolysed by heating for 1 h a 60° C. in the presence of aqueous 30% sodium hydroxide solution. Crude 1-phenyl-4-methylpyrazole, identified by $^1$H NMR and mass spectrometry, is recovered by phase separation. A determination performed on the crude product shows that 1-phenyl-4-methylpyrazole has been formed in a 65% yield.

EXAMPLE 6

Synthesis of 1-methyl-4-phenylpyrazole from 2-benzyl-1,3-dioxolane, N,N-dimethylchloromethyliminium chloride and monomethylhydrazine.

32.8 g (0.20 mol) of 2-benzyl-1,3-dioxolane are introduced, at a temperature of between 50° C. and 65° C., into a reactor containing 57.6 g (0.45 mol) of N,N-dimethylchloromethyliminium chloride in solution in 150 ml of chloroform and the solution is then heated for 1 h to 65° C. The chloroform is removed under reduced pressure and 11.5 g (0.25 mol) of monomethylhydrazine in aqueous solution at a concentration of 30% are then introduced at 50° C. The solution is heated for 2 h at 70° C. It is cooled to 20° C. and then neutralised to pH =8 with an aqueous 30% sodium hydroxide solution. 10 ml of water are then added and the required product is then extracted with 2 15-ml portions of methylene chloride. The extraction solvent is removed. A crude product is thus obtained, which was purified by recrystallisation from isopropyl ether. The purified product, 1-methyl-4-phenylpyrazole, identified by $^1$H NMR and mass spectrometry, has a melting point of 103.6° C. The yield of 1-methyl-4-phenylpyrazole formed, determined by quantitative analysis of the crude product, is 46%.

We claim:

1. Process for the synthesis of 1,4-disubstituted pyrazoles, characterised in that a monosubstituted hydrazine is reacted with the product of reaction of an acetal with an N-substituted halomethyliminium salt.

2. Process for synthesis according to claim 1, characterised in that the acetal corresponds to the general formula (I)

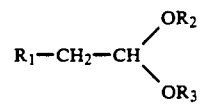

the monosubstituted hydrazine to the general formula (II) $R_4NH-NH_2$, and the 1,4-disubstituted pyrazoles obtained to the general formula (III)

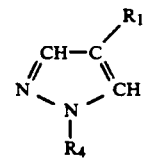

in which formulae:

$R_1$ and $R_4$, which are identical or different, denote:
a substituted or unsubstituted, linear or branched, aliphatic radical, a substituted or unsubstituted aryl radical, $R_2$ and $R_3$, which are identical or different, denote a substituted or unsubstituted, linear or branched, aliphatic radical, or else $R_2$ and $R_3$, together with the two oxygen atoms to which they are linked and the carbon atom situated between these two oxygen atoms, form a substituted or unsubstituted ring containing 3 to 49 carbon atoms.

3. Process for the synthesis of 1,4-disubstituted pyrazoles according to claim 2, characterised in that $R_1$ and $R_4$, which are identical or different, denote a $C_1$-$C_{12}$ alkyl radical or an optionally substituted phenyl radical.

4. Process for the synthesis of 1,4-disubstituted pyrazoles according to claim 2 characterised in that $R_2$ and $R_3$, which are identical or different, denote a $C_1$-$C_{12}$ alkyl radical, or else $R_2$ and $R_3$, together with the 2 oxygen atoms to which they are linked and the carbon atom situated between these 2 oxygen atoms, form a ring containing 3 to 7 carbon atoms.

5. Process for the synthesis of 1,4-disubstituted pyrazoles according to claim 1 characterised in that the N-substituted halomethyliminium salt is an N-substituted halomethyliminium halide.

6. Process for the synthesis of 1,4-disubstituted pyrazoles according to claim 5, characterised in that the N-substituted halomethyliminium halide corresponds to the general formula (IV):

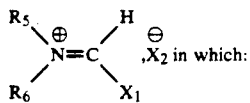

$X_1$ and $X_2$, which are identical or different, denote a chlorine or bromine atom, $R_5$ denotes:
 a substituted or unsubstituted, linear or branched, aliphatic radical, a substituted or unsubstituted aryl radical, $R_6$ denotes:
 hydrogen,
 a substituted or unsubstituted, linear or branched, aliphatic radical, a substituted or unsubstituted aryl, radical,
 or else $R_5$ and $R_6$, together with the nitrogen atom to which they are linked, form a substituted or unsubstituted ring containing 3 to 48 carbon atoms.

7. Process for the synthesis of 1,4-disubstituted pyrazoles according to claim 5 characterised in that the N-substituted halomethyliminium halide is an N-substituted chloromethyliminium chloride.

8. Process for the synthesis of 1,4-disubstituted pyrazoles according to claim 5 characterised in that the N-substituted halomethyliminium halide is obtained in situ in the reaction mixture by the reaction of at least one halogenating agent with an N-substituted amide.

9. Process for the synthesis of 1,4-disubstituted pyrazoles according to claim 8, characterised in that the halogenating agent is a chlorinating agent chosen from the group consisting of $COCl_2$, $(COCl)_2$, $SOCl_2$ and mixtures thereof.

10. Process of synthesis according to claim 1 characterised in that the reaction of the acetal with the N-substituted halomethyliminium salt is carried out in an organic solvent at a temperature of between 20° and 150° C.

11. Process of synthesis to claim 1 characterised in that the molar ratio of the N-substituted halomethyliminium salt to the acetal is between 1.5 and 3 and the molar ratio of the monosubstituted hyrazine to the acetal is between 0.8 and 2.

12. Process of synthesis according to claim 8 characterised in that the molar ratio of the halogenating agent to the acetal is between 1.4 and 4, the molar ratio of the N-substituted amide to the acetal is between 0.8 and 3 and the molar ratio of the monosubstituted hydrazine to the acetal is between 0.8 and 2.

13. Process for the synthesis of 1,4-disubstituted pyrazoles according to claim 1 characterised in that after the reaction of the monosubstituted hydrazine with the product of reaction of the acetal with the N-substituted halomethyliminium salt the mixture is neutralised with a basic aqueous solution, the 1,4-disubstituted pyrazole is extracted with an organic solvent, the extraction solvent is removed and the crude product obtained is then purified.

14. Process for the synthesis of 1,4-disubstituted pyrazoles according to claim 13, characterised in that the crude product obtained is treated with a concentrated alkaline aqueous solution at a temperature of between 40° C. and 70° C.

* * * * *